(12) United States Patent
Fang et al.

(10) Patent No.: US 11,504,406 B2
(45) Date of Patent: Nov. 22, 2022

(54) PROBIOTIC AND PROBIOTIC COMBINATION FOR INHIBITION OF VANCOMYCIN-RESISTANT ENTEROCOCCI AND USE THEREOF

(71) Applicants: Delta Electronics, Inc., Taoyuan (TW); Taipei Medical University, Taipei (TW)

(72) Inventors: Shiuh-Bin Fang, Taipei (TW); Kun-Nan Tsai, Taoyuan (TW); Wei-Sheng Sun, Taipei (TW); Yu-Hsuan Ho, Taoyuan (TW); Yuarn-Jang Lee, Taipei (TW)

(73) Assignees: DELTA ELECTRONICS, INC., Taoyuan (TW); TAIPEI MEDICAL UNIVERSITY, Taipei (TW)

( * ) Notice: Subject to any disclaimer, the term of this patent is extended or adjusted under 35 U.S.C. 154(b) by 23 days.

(21) Appl. No.: 16/818,661

(22) Filed: Mar. 13, 2020

(65) Prior Publication Data
US 2021/0060092 A1  Mar. 4, 2021

(30) Foreign Application Priority Data
Sep. 4, 2019  (CN) .......................... 201910831024.4

(51) Int. Cl.
*A61K 35/742*  (2015.01)
*A61K 9/48*  (2006.01)

(52) U.S. Cl.
CPC .......... *A61K 35/742* (2013.01); *A61K 9/4866* (2013.01)

(58) Field of Classification Search
None
See application file for complete search history.

(56) References Cited

U.S. PATENT DOCUMENTS

| | | | |
|---|---|---|---|
| 6,645,530 B1 * | 11/2003 | Borody ................. | A61K 35/74 424/543 |
| 6,849,256 B1 * | 2/2005 | Farmer .................... | A61P 1/00 424/93.46 |
| 9,028,841 B2 | 5/2015 | Henn et al. | |
| 2005/0232909 A1 | 10/2005 | Farmer et al. | |
| 2016/0243172 A1 | 8/2016 | Cook et al. | |
| 2017/0151291 A1 | 6/2017 | Henn et al. | |
| 2018/0256653 A1 | 9/2018 | Pamer et al. | |

FOREIGN PATENT DOCUMENTS

| | | | |
|---|---|---|---|
| CN | 104582712 | A | 4/2015 |
| CN | 108338993 | * | 7/2017 |
| CN | 108135944 | A | 6/2018 |
| TW | 200902040 | A | 1/2009 |

OTHER PUBLICATIONS

Xanthopoulos et al. Food Microbiology, 2000, 17, pp. 205-215.*
Zhang et al. (2016), Screening probiotic strains for safety: Evaluation of virulence and antimicrobial susceptibility of enterococci from healthy Chinese infants, Journal of Dairy Science, 99(6), 4282-4290.
Submuth et al.. Aggregation Substance Promotes Adherence, Phagocytosis, and Intracellular Survival of Tnterococcus faecalis within Human Macrophages and Suppresses Respiratory Burst, American Society for Microbiology, Infection and Immunity, Sep. 2000, p. 4900-4906, vol. 68, No. 9.
Nallapareddy et al.. Clinical isolates of Enterococcus Faecium exhibit strain-specific collagen binding mediated by Acm, a new member of the MSCRAMM family; Molecular Microbiology (2003) 47(6), 1733-1747.
Manley et al., Probiotic treatment of vanconmycin-resistant enterococci: a randomised controlled trial, MJA, pp. 454-457, vol. 186, No. 9, May 7, 2007.
Caporaso et al., QIIME allows analysis of high-throughput community sequencing data, NIH Public Access Author Manuscript, National Institutes of Health, Nat Methods. May 2010; 7(5) 335-336.
De Regt et al., Effects of Probiotics on Acquisition and Spread of Multiresistant Enterococci, American Society for Microbiology, Antimicrobial Agents and Chemotherapy, Jul. 2010, p. 2801-2805.
Vidal et al., Probiotics and Intestinal Colonization by Vancomycin-Resistant Enterococci in Mice and Humans, American Society for Microbiology, Journal of Clinical Microbiology, Jul. 2010, p. 2595-2598, vol. 48, No. 7.
Szachta et al., An Evaluation of the Ability of the Probiotic Strain Lactobacillus rhamnosus GG to Eliminate the Gastrointestinal Carrier State of Vancomycin-resistant Enterococci in Colonized Children, J Clin Gastroenterol, vol. 45, No. 10, Nov./Dec. 2011, pp. 872-877.
Doron et al., Effect of Lactobacillus rhamnosus GG Administration on Vancomycin-Resistant Enterococcus Colincation in Adults with Comorbidities, American Society of Microbiology, Antimicrobial Agents and Chemotherapy, Aug. 2015, vol. 59., No. 8. pp. 4593-4599.
Topcuoglu et al., A new risk factor for neonatal vancomycin-resistant Enterococcus colonisation: bacterial probiotics, The Journal of Maternal-Fetal & Neonatal Medicine, Sep. 19, 2014.
Tsai et al., Inferring microbial interaction network from microbiome data using RMN algorithm, BMC Systems Biology (2015) 9:54.
C.J. Donskey et al., Effect of oral Bacillus coagulans administration on the density of vancomycin-resistant enterococci in the stool of colonized mice, Letters in Applied Microbiology 2001, 33, 84-88.

* cited by examiner

*Primary Examiner* — Vera Afremova
(74) *Attorney, Agent, or Firm* — Kirton McConkie; Evan R. Witt

(57) ABSTRACT

A probiotic combination for inhibition of vancomycin-resistant enterococci includes *Bacillus coagulans*, *Lactobacillus rhamnosus* CG, *Lactobacillus reuteri*, and *Lactobacillus acidophilus*. The probiotic combination can inhibit growth, host cell attachment, or virulence of vancomycin-resistant enterococci, and also can inhibit virulence gene expression of vancomycin-resistant enterococci. The virulence gene includes at least one of asa1, acm, ebpA, ebpB, ebpC, efaA, sagA, esp, sgrA, and scm genes.

7 Claims, 30 Drawing Sheets

PROBIOTIC AND PROBIOTIC COMBINATION FOR INHIBITION OF VANCOMYCIN-RESISTANT ENTEROCOCCI AND USE THEREOF

FIELD OF THE INVENTION

The present invention relates to a probiotic combination, and more particularly to a probiotic combination for inhibition of vancomycin-resistant enterococci.

BACKGROUND OF THE INVENTION

Enterococci belong to the commensal bacteria in the human gut, harmless to healthy individuals, but may cause opportunist infections in immunocompromised patients, such as patients having serious potential disease, low white blood cell count, urethral or vascular catheter placement, or long hospital stay. The opportunist infection may cause urinary tract infection, myocarditis, meningitis, or sepsis, which may not be effectively treated by advanced antibiotics and thus results in serious medical problems. The proportions of vancomycin-resistant enterococci (VRE) found in worldwide clinical enterococci isolates are 4.0% in Europe, 6.0% in Canada, 11.9% in Asia, 12.9% in South America, and 35.5% in the United States. The VRE carrier rate in the intensive care units has increased to 4.4%-12.3% in recent years. In Taiwan, the first VRE clinical isolate was reported in 1996, and in the annual report of Taiwan Opportunistic Infection Surveillance System in 2013, up to 28.7% of the enterococci isolates from the patients in the intensive care units were resistant to vancomycin, and in one medical center in Taiwan, the new VRE incidence is up to 21.9 people per 1,000 days of stay, showing that VRE has become a major threat to worldwide human health and medical care.

In recent years, there have been a few studies about exploiting probiotics to remove colonization of VRE in the human gut, but the used probiotic strains were not identical and it was not conclusive whether they were effective or not. For example, *Lactobacillus rhamnosus* GG (LGG) had successfully eliminated VRE colonization in the human gut in two clinical trials (Manley et al. (2007) Med J Aust 186: 454-457; Szachta et al. (2011) J Clin Gastroenterol 45: 872-877), but in another small trial, there was no effective eliminating effect (Doron et al. (2015) Antimicrob Agents Chemother. 59(8): 4593-9). In addition, another strain of *Lactobacillus rhamnosus* Lcr35 did not show clear effects in a small adult trial (Vidal et al. (2010) J Clin Microbiol 48: 2595-2598). Two other studies showed that multiple combinations of probiotic strains had no preventive effect on VRE colonization in the human gut, and there were even concerns about the transfer of resistance genes of bacteria may be mediated by probiotics (de Regt et al. (2010) Antimicrob Agents Chemother 54: 2801-2805; Topcuoglu et al. (2015) J Matern Fetal Neonatal Med 28: 1491-1494).

Since these few clinical trials used different strains, doses, durations, and research methods, there is still a need to find out a probiotic combination which can effectively inhibit or remove VRE colonization.

SUMMARY OF THE INVENTION

An object of the present invention is to provide a probiotic combination which can inhibit growth, host cell attachment, or virulence of vancomycin-resistant enterococci, so as to reduce the harm of vancomycin-resistant enterococci to the human body.

In accordance with an aspect of the present invention, there is provided a method for inhibiting growth, host cell attachment, or virulence of vancomycin-resistant enterococci by administrating a probiotic combination including *Bacillus coagulans, Lactobacillus rhamnosus* GG, *Lactobacillus reuteri*, and *Lactobacillus acidophilus*.

In an embodiment, the probiotic combination inhibits virulence gene expression of the vancomycin-resistant enterococci. The virulence gene includes at least one of asa1, acm, ebpA, ebpB, ebpC, efaA, sagA, esp, sgrA, and scm genes.

In an embodiment, the probiotic combination inhibits the vancomycin-resistant enterococci from attaching to human intestinal epithelial cells.

In an embodiment, the vancomycin-resistant enterococci include *Enterococcus faecium* and *Enterococcus faecalis*.

In an embodiment, the probiotic combination is prepared as a probiotic capsule, and the probiotic capsule includes an excipient. The excipient is corn starch.

In accordance with another aspect of the present invention, there is provided a probiotic combination for inhibition of vancomycin-resistant enterococci, wherein the probiotic combination includes *Bacillus coagulans, Lactobacillus rhamnosus* GG, *Lactobacillus reuteri*, and *Lactobacillus acidophilus*.

In an embodiment, the probiotic combination inhibits growth of the vancomycin-resistant enterococci.

In an embodiment, the probiotic combination inhibits the vancomycin-resistant enterococci from attaching to human intestinal epithelial cells.

In an embodiment, the probiotic combination inhibits virulence gene expression of the vancomycin-resistant enterococci. The virulence gene includes at least one of asa1, acm, ebpA, ebpB, ebpC, efaA, sagA, esp, sgrA, and scm genes.

In an embodiment, the vancomycin-resistant enterococci include *Enterococcus faecium* and *Enterococcus faecalis*.

In an embodiment, the probiotic combination is prepared as a probiotic capsule, and the probiotic capsule includes an excipient. The excipient is corn starch.

In accordance with a further aspect of the present invention, there is provided a medicine and health product including a probiotic combination for inhibition of vancomycin-resistant enterococci, wherein the probiotic combination includes *Bacillus coagulans, Lactobacillus rhamnosus* GG, *Lactobacillus reuteri*, and *Lactobacillus acidophilus*.

In an embodiment, the probiotic combination inhibits growth of the vancomycin-resistant enterococci.

In an embodiment, the probiotic combination inhibits the vancomycin-resistant enterococci from attaching to human intestinal epithelial cells.

In an embodiment, the probiotic combination inhibits virulence gene expression of the vancomycin-resistant enterococci. The virulence gene includes at least one of asa1, acm, ebpA, ebpB, ebpC, efaA, sagA, esp, sgrA, and scm genes.

The above contents of the present invention will become more readily apparent to those ordinarily skilled in the art after reviewing the following detailed description and accompanying drawings, in which:

DETAILED DESCRIPTION OF THE PREFERRED EMBODIMENT

The present invention will be described more specifically with reference to the following embodiments. It is to be noted that the following descriptions of preferred embodiments of this invention are presented herein for purpose of illustration and description only. It is not intended to be exhaustive or to be limited to the precise form disclosed.

The present invention uses a microbial network analysis driven by rule-based network algorithm combined with biological experiments to select a probiotic combination which can effectively inhibit the growth, host cell attachment, or virulence of vancomycin-resistant enterococci (VRE), and inhibit the virulence gene expression of VRE. The probiotic combination includes *Bacillus coagulans, Lactobacillus rhamnosus* GG, *Lactobacillus reuteri*, and *Lactobacillus acidophilus*. The probiotic combination can effectively inhibit VRE growth in vitro, significantly inhibit expressions of VRE virulence genes, and reduce VRE attachment to human intestinal epithelial cells. The probiotic combination provided in the present invention will contribute to clinical treatment and VRE decolonization from the host gut, thereby reducing the harm of VRE to the human body.

Figure 1:
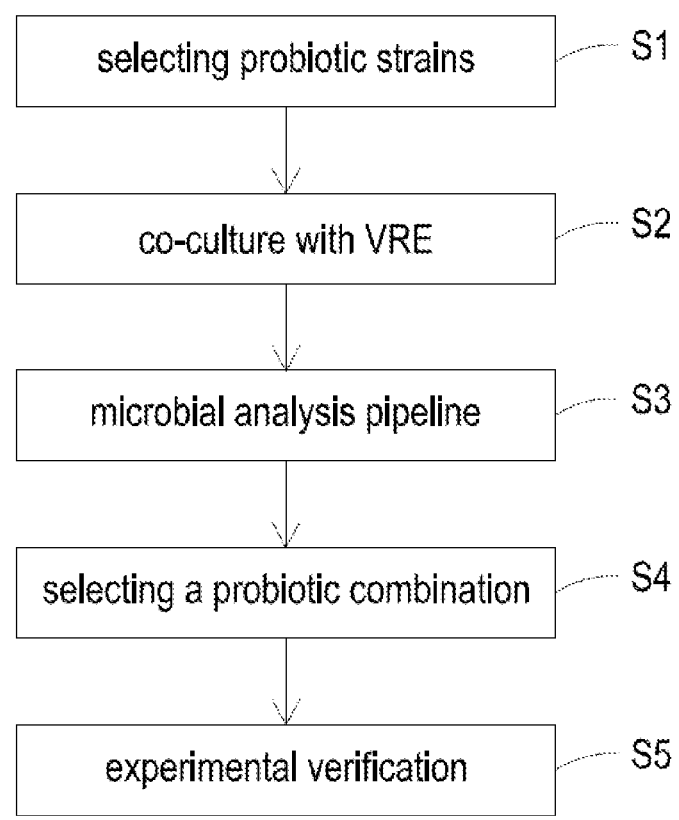
FIG. 1 shows a flow chart of the method for selecting a probiotic combination of the present invention.

The following embodiments will further illustrate the method of selecting the probiotic combination in the present invention and the related experimental verification. FIG. 1 shows a flow chart of the method for selecting a probiotic combination of the present invention. As shown in FIG. 1, the method for selecting a probiotic combination includes steps of selecting probiotic strains (step S1), co-culture with VRE (step S2), microbial analysis pipeline (step S3), selecting a probiotic combination (step S4), and experimental verification (step S5). The steps are respectively described below.

First, the VRE strains used in the present invention were clinical isolates from Taipei Medical University Hospital and Shuang Ho Hospital. The resistance to vancomycin was confirmed by a disc diffusion assay, and the presence of the drug resistance genes including vanA, vanB, van C, vanD, vanE, and vanG was confirmed by PCR. The VRE includes at least two strains, which are *Enterococcus faecium* and *Enterococcus faecalis*, respectively.

In step S1, in order to achieve the diversity of microbial species, the present invention selected the strains of probiotic bacteria from the edible probiotic strains listed in the Food and Drug Administration of Taiwan Ministry of Health and Welfare by classification and considering the availability of the strains and the feasibility of co-culture. The ten probiotic strains listed in Table 1 were initially selected. Further, the supplementary information regarding the probiotic strains are generally recognized as safe (GRAS) by the Food and Drug Administration of the United States is also provided in Table 1.

TABLE 1

| No. | Probiotic Strain | GRAS information |
|---|---|---|
| 1 | *Bacillus coagulans* | https://www.fda.gov/media/104471/download |
| 2 | *Bifidobacterium bifidum* | https://www.fda.gov/media/116006/download |
| 3 | *Bifidobacterium longum* subsp. *infantis* | https://www.fda.gov/media/116006/download |
| 4 | *Lactobacillus rhamnosus* GG | https://www.fda.gov/media/134877/download |
| 5 | *Lactococcus lactis* subsp. *lactis* | https://www.fda.gov/food/generally-recognized-safe-gras/microorganisms-microbial-derived-ingredients-used-food-partial-list |
| 6 | *Lactobacillus plantarum* subsp. *plantarum* | https://www.fda.gov/media/132055/download |
| 7 | *Lactobacillus reuteri* | https://www.accessdata.fda.gov/scripts/fdcc/?set=GRASNotices&id=409 |
| 8 | *Sporolactobacillus inulinus* | |
| 9 | *Streptococcus salivarius* subsp. *thermophilus* | https://www.fda.gov/food/gras-notice-inventory/agency-response-letter-gras-notice-no-grn-000591 |
| 10 | *Lactobacillus acidophilus* | https://www.fda.gov/media/134215/download |

Figure 2:
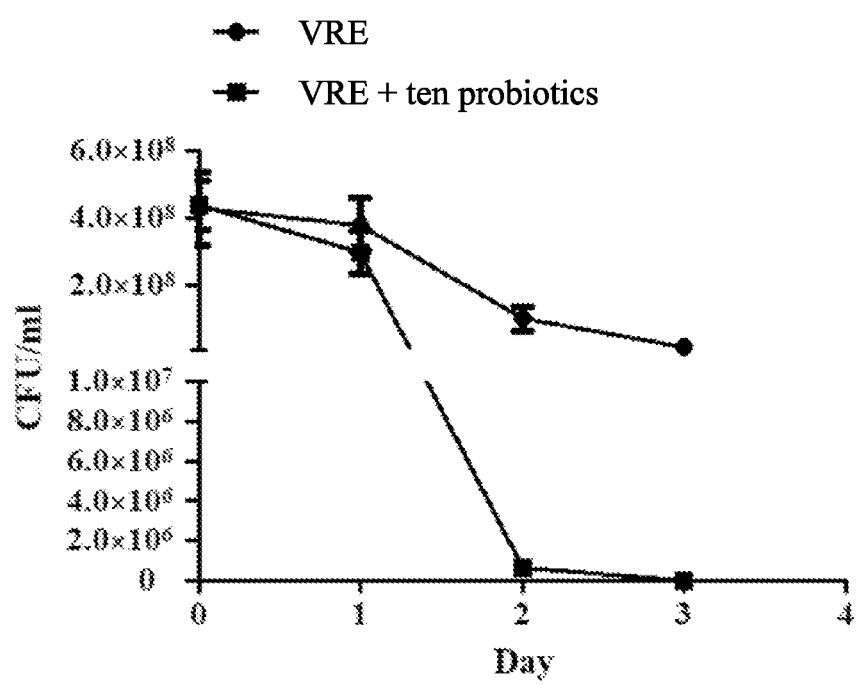
FIG. 2 shows the results of co-culture of the VRE with the ten probiotics.

Next, in step S2, the ten probiotics were incubated with agitation, and then, the probiotics, with an individual amount of $1 \times 10^8$ CFU, were mixed and co-cultured with the VRE for a certain period of time. During the co-culture of the probiotics and the VRE, the VRE were quantified by CHROM VRE agar to evaluate whether the ten probiotics could effectively inhibit VRE. FIG. 2 shows the results of co-culture of the VRE with the ten probiotics. As shown in FIG. 2, compared with the VRE culture without probiotics, the bacterial amounts (CFU/mL) of the VRE in the VRE-probiotic co-culture were decreased significantly on the second day of co-culture, and there was almost no survival VRE on the third day, indicating that these ten probiotics effectively inhibited the growth of the VRE.

The bacterial pellets at the eleven time points within three days of the VRE-probiotic co-culture were collected in duplicate for genomic DNA isolation. The 16s rDNA of all the bacteria strains were identified and quantified by Next Generation Sequencing (NGS) technique.

Figure 3:
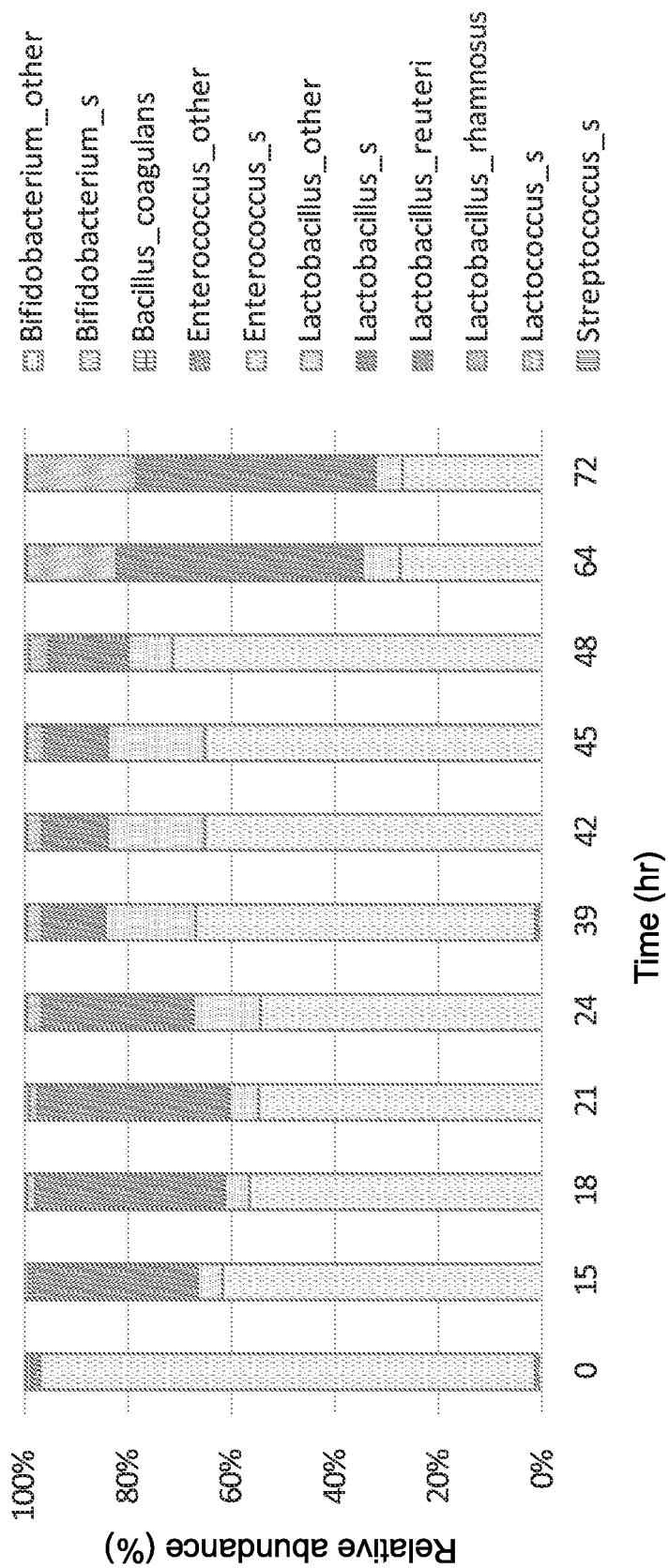
FIG. 3 shows the relative abundance of individual bacterial population in the VRE-probiotic co-culture.

Next, in step S3, all the bacteria strains and their relative abundance at individual time points were further analyzed by microbiome analysis pipeline (MAP) technique with the analysis software QIIME (Caporaso et al. (2010) Nat Methods. 7(5): 335-336). FIG. 3 shows the relative abundance of individual bacterial population in the VRE-probiotic co-culture. The relative proportion of individual bacterial population in total population at the selected time points were observed, wherein *Enterococcus*_s represents VRE, *Lactobacillus*_s represents *L. plantarum* or *L. acidophilus*, and *Lactobacillus*_rhamnosus represents LGG. In addition, one of the probiotic strains, *Sporolactobacillus inulinus*, was originally added in the experiment but not classified by QIIME in NGS analysis, so there was no such a strain in FIG. 3.

Figure 4:
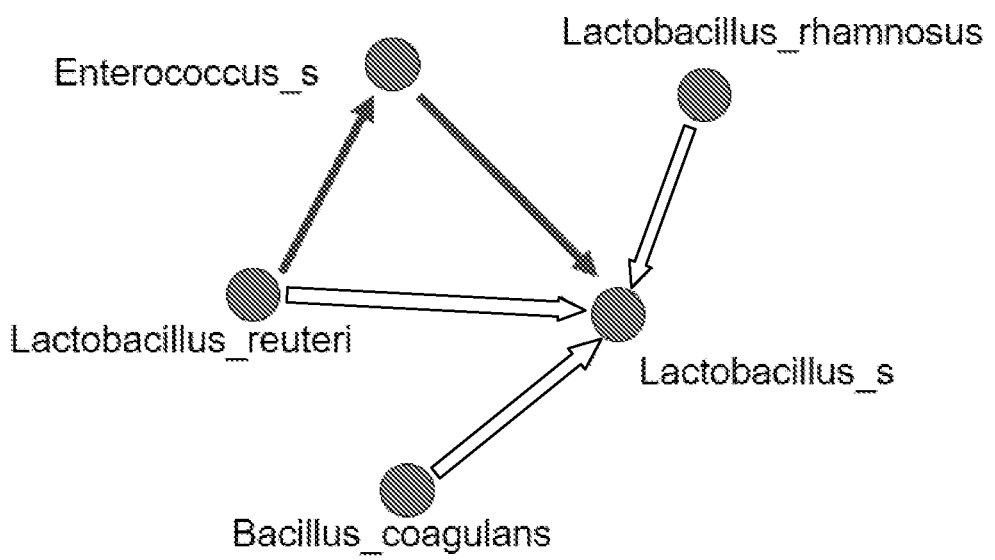
FIG. 4 shows the predicted microbial interaction network.

After obtaining the relative abundance of individual bacterial population at the selected time points, a rule-based microbial network (RMN) algorithm (Tsai et al. (2015) BMC Syst Biol 9: 54) was used to analyze the relative abundance of any three microorganisms. As a result, the cooperative relationships and the competitive relationships between microorganisms were obtained, thereby generating a microbial interaction network. FIG. 4 shows the predicted microbial interaction network, wherein the solid arrow indicates an inhibitory effect and the open arrow indicates an assisting effect. Accordingly, the present invention predicted the cooperative relationships and the competitive relationships between the VRE and the probiotics, and also predicted the cooperative relationships and the competitive relationships between the probiotics by RMN. Subsequently, by removing the probiotics which have cooperative relationships with the VRE and removing the probiotics which have competitive relationships with the probiotics, a probiotic combination having a VRE inhibitory effect shown in FIG. 4 was selected (step S4). The probiotic combination includes *Bacillus coagulans*, *Lactobacillus rhamnosus* GG (LGG), *Lactobacillus reuteri*, and *Lactobacillus*_s.

Next, in step S5, the inhibitory effect of the probiotic combination on VRE growth was verified by in vitro experiments.

Figure 5:
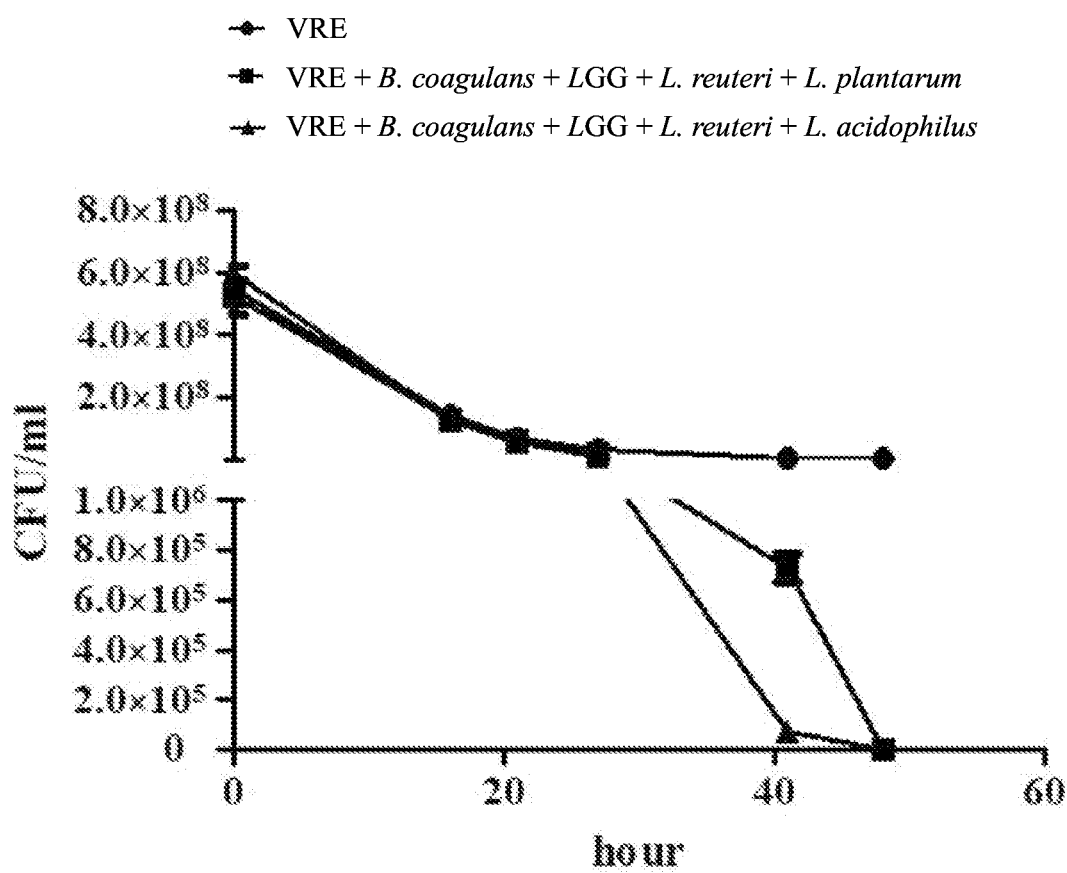
FIG. 5 shows the co-culture result of the VRE and the probiotic combinations including *L. acidophilus* or *L. plantarum*.

First, since *Lactobacillus*_s includes *L. plantarum* and *L. acidophilus*, in order to confirm which one of *L. plantarum* and *L. acidophilus* is more effective, the inhibitory effects of these two strains, *L. plantarum*_ATCC14917 and *L. acidophilus*_Infloran, against VRE population in co-culture model were compared in the combination with *B. coagulans*_ATCC7050, LGG_Hansen, and *L. reuteri*_BioGaia. The four strains were combined in equal ratio, and during the co-culture, the VRE were also quantified by CHROM VRE agar. FIG. 5 shows the co-culture result of the VRE and the probiotic combinations including *L. acidophilus* or *L. plantarum*. According to the result of FIG. 5, the combination of *B. coagulans*, LGG, *L. reuteri*, and *L. acidophilus* was more effective than the combination of *B. coagulans*, LGG, *L. reuteri*, and *L. plantarum* in inhibiting VRE growth.

The result also demonstrated that the probiotic combination inferred by RMN can indeed inhibit the growth of the VRE.

Since *L. acidophilus* has a better inhibitory effect on VRE growth than *L. plantarum*, the four probiotics of *B. coagulans*, LGG, *L. reuteri*, and *L. acidophilus* were selected as the probiotic combination in the present invention.

In order to use these four probiotics for clinical trials and develop potential products in the future, the probiotic strains from different sources, including *B. coagulans*_BC1031, LGG_DSMZ32250, *L. reuteri*_BR101, and *L. acidophilus*_LA1063 were additionally purchased for further experiments. The four purchased strains were compared with the original four edible strains for 16s rDNA sequence. According to the sequence alignment, *B. coagulans*_ATCC7050 and *B. coagulans*_BC1031 have 99% sequence identity in the V3-V4 region of 16s rDNA; LGG_Hansen and LGG_DSMZ32250 have 100% sequence identity in the V3-V4 region of 16s rDNA; *L. reuteri*_BioGaia and *L. reuteri*_BR101 have 100% sequence identity in the V3-V4 region of 16s rDNA; and *L. acidophilus*_Infloran and *L. acidophilus*_LA1063 have 100% sequence identity in the V3-V4 region of 16s rDNA. In other words, the strains from different sources have almost the same sequence in the V3-V4 region of 16s rDNA, so it is predicted that the strains from different sources also exert the same inhibitory effects.

Figure 6:
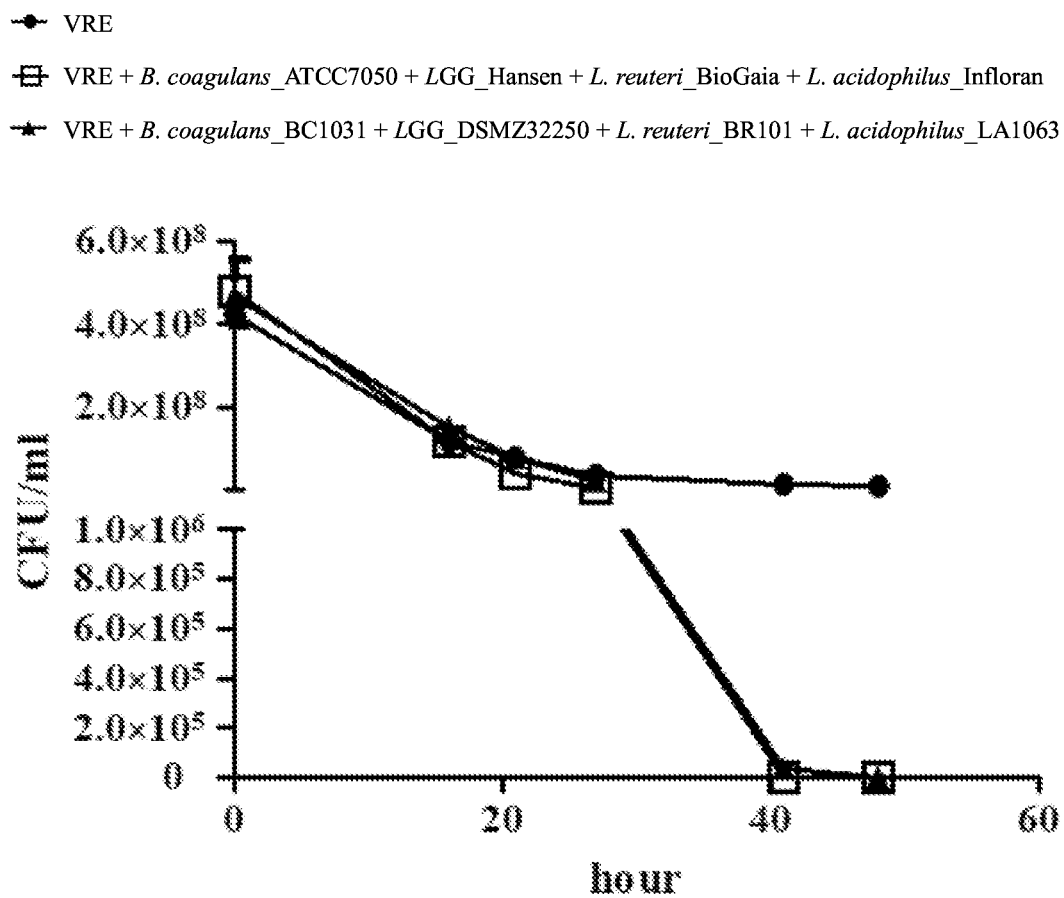
FIG. 6 shows the co-culture result of the VRE and the probiotic combinations from different sources.

FIG. 6 shows the co-culture result of the VRE and the probiotic combinations from different sources, wherein the four strains were combined in equal ratio. According to the result of FIG. 6, the probiotic combinations for the four strains of *B. coagulans*, LGG, *L. reuteri* and *L. acidophilus* from different sources had almost the same inhibitory effects. The result also demonstrated that the inhibitory effect of the probiotic combination is not limited to the strains from specific sources.

Figure 7:
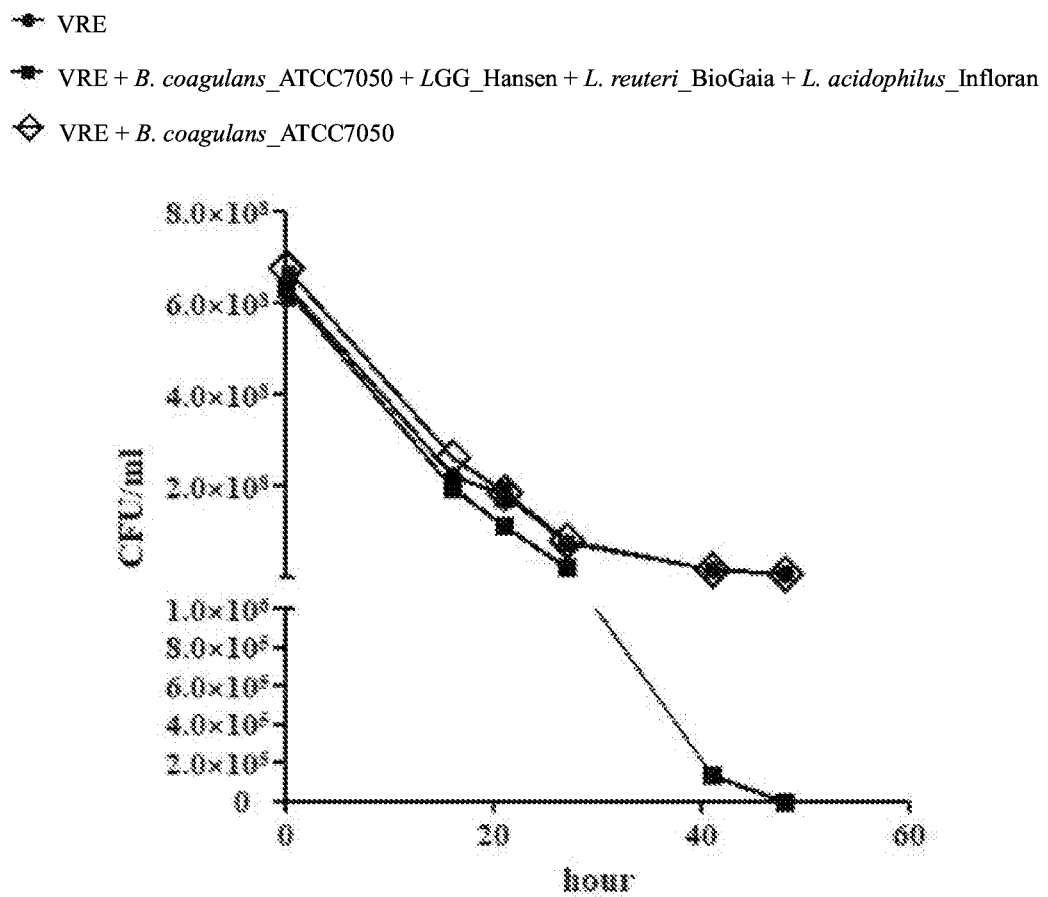
FIGS. 7 to 11 show the co-culture results of the VRE with the probiotic combinations of the four strains or the individual strains.
Figure 8:
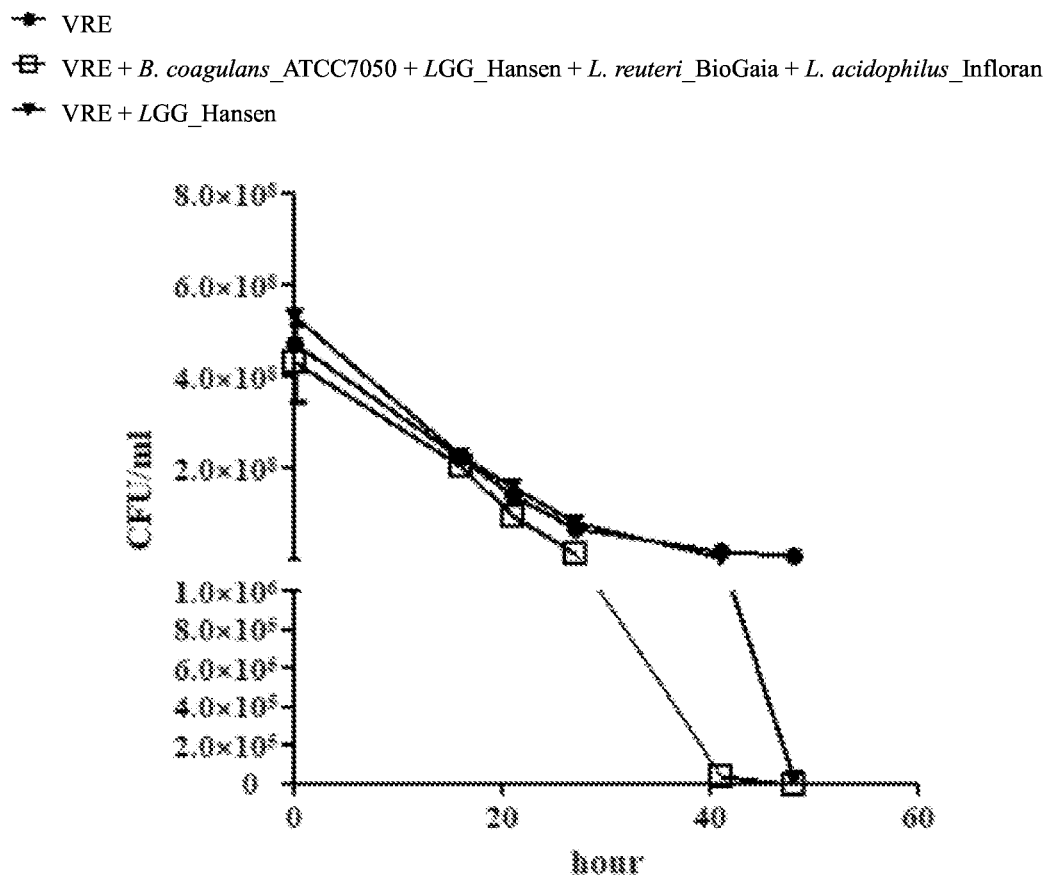
Figure 9:
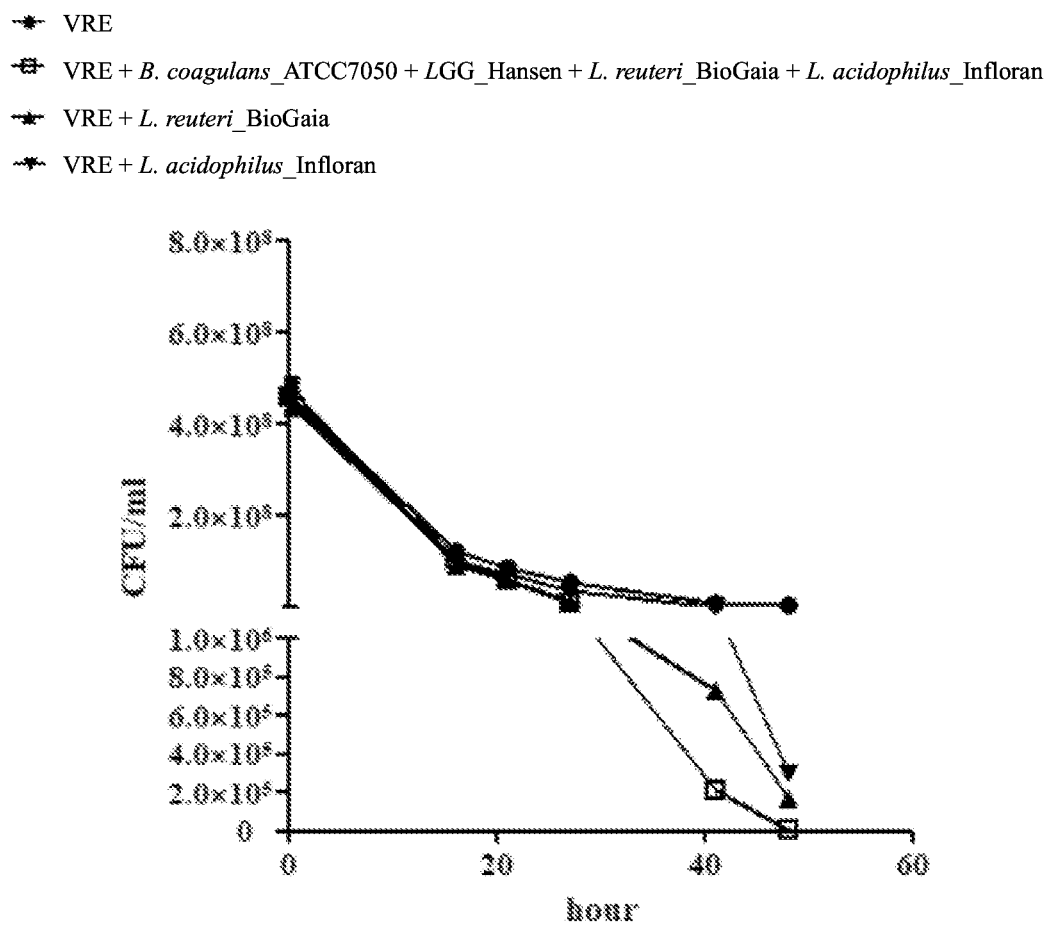
Figure 10:
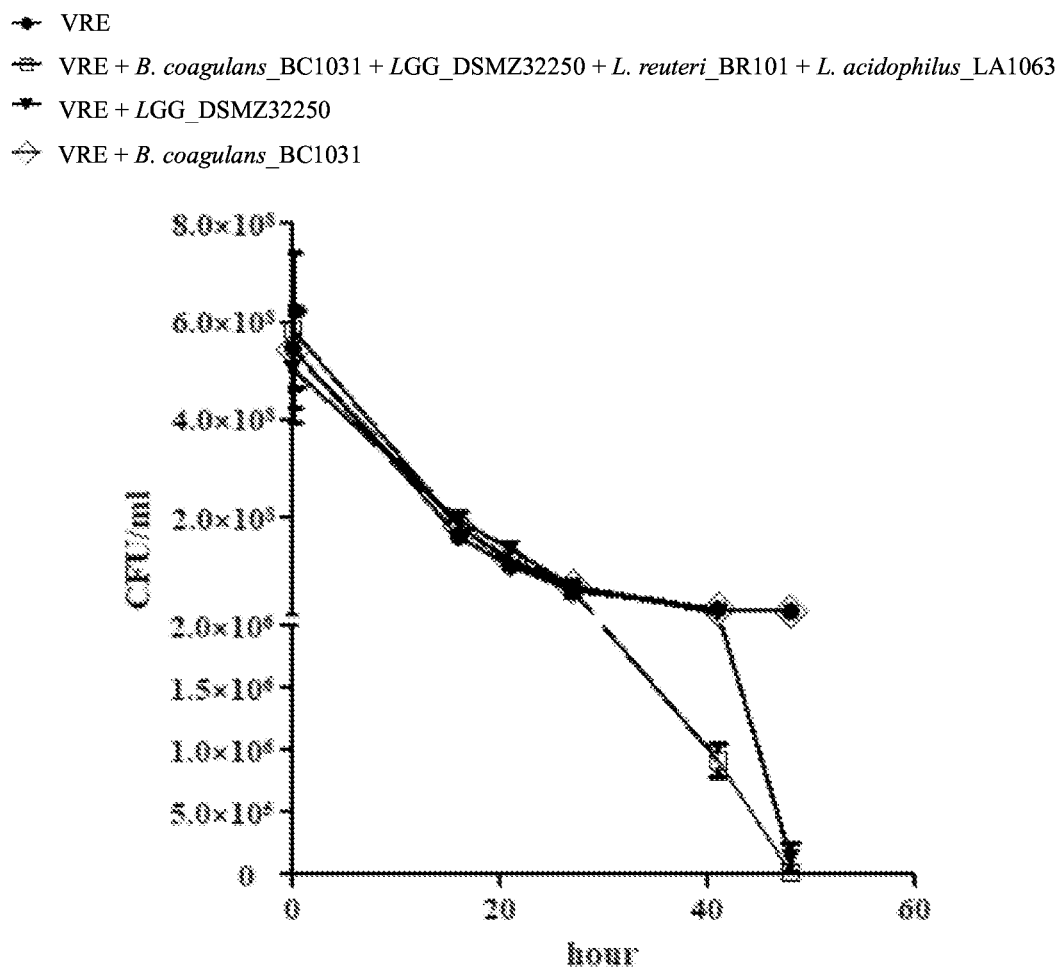
Figure 11:
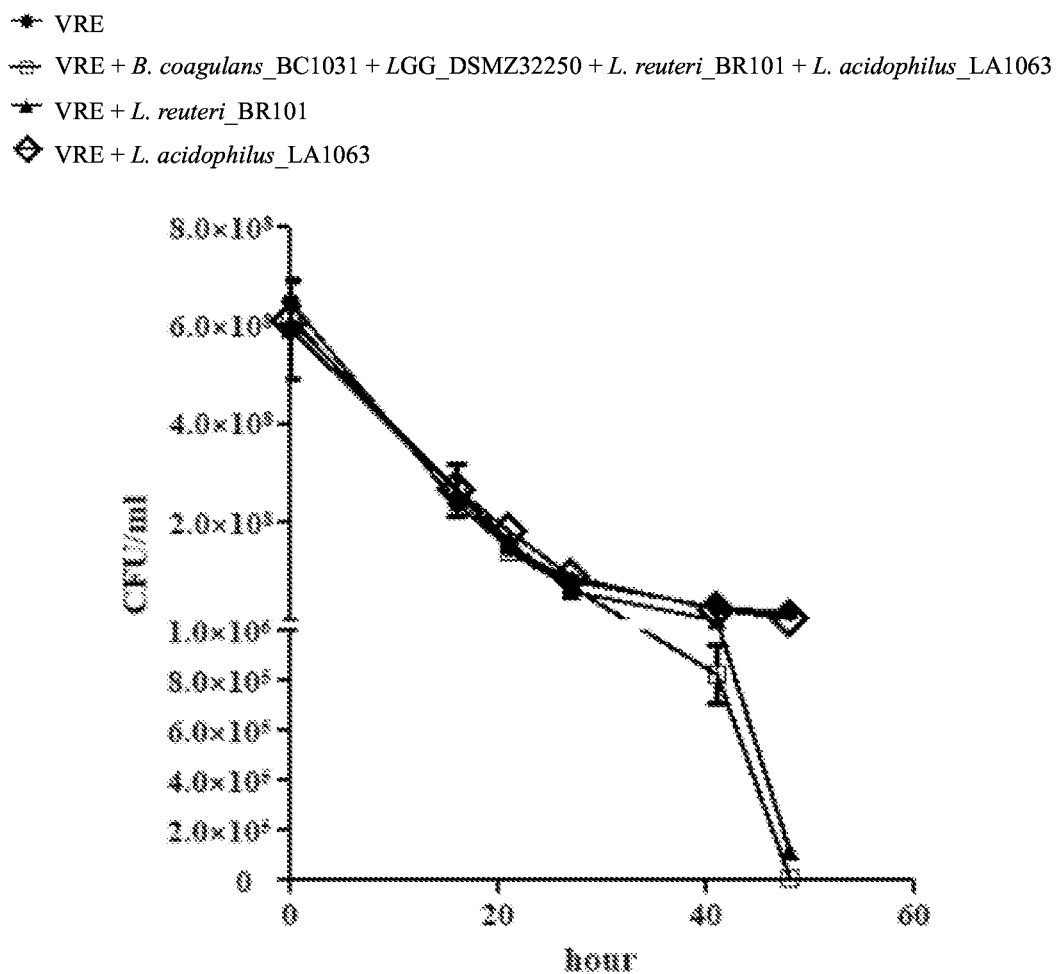

Further, the inhibitory effects of the probiotic combinations of the four strains combined in equal ratio were compared with the inhibitory effects of the individual strains, wherein the total bacteria amount were all the same ($4 \times 10^8$ CFU). FIGS. 7 to 11 show the co-culture results of the VRE with the probiotic combinations of the four strains or the individual strains. According to the results of FIGS. 7 to 11, either the probiotic combination of *B. coagulans*_ATCC7050, LGG_Hansen, *L. reuteri*_BioGaia, and *L. acidophilus*_Infloran or the probiotic combination of *B. coagulans*_BC1031, LGG_DSMZ32250, *L. reuteri*_BR101, and *L. acidophilus*_LA1063 had better VRE inhibitory effects than individual strains did. The single strain of *B. coagulans*_ATCC7050 did not inhibit the growth of the VRE (as shown in FIG. 7). The individual strains of LGG_Hansen, *L. reuteri*_BioGaia, and *L. acidophilus*_Infloran had an inhibitory effect on VRE growth, but the inhibition was slower than that of the probiotic combination (as in FIG. 8 and FIG. 9). The single strain of *B. coagulans*_BC1031 did not inhibit the growth of the VRE, and the inhibitory effect of the single strain of LGG_DSMZ32250 was inferior to that of the probiotic combination of the four strains, and the number of the VRE was not significantly reduced until 48 hours (as shown in FIG. 10). The inhibitory effect of the single strain of *L. reuteri*_BR101 was not as good as the probiotic combination of the four strains at the time point of 41 hour, whereas the single strain of *L. acidophilus*_LA1063 did not inhibit the growth of the VRE (as shown in FIG. 11). Therefore, the probiotic combination of the four strains including *B. coagulans*, LGG, *L. reuteri*, and *L. acidophilus* had a better inhibitory effect on the growth of the VRE than the individual strains did, which confirms that the probiotic combination provided in the present invention can significantly inhibit the growth of the VRE in in vitro experiments.

In order to find out the preferred combination ratios of the four probiotic strains for further application in clinical trials, the four strains were combined in different ratios and co-cultured with the VRE to compare the VRE inhibitory effects in different combination ratios. Since the predicted microbial interaction network of FIG. 4 shows that *L. reuteri* was the predominant strain to inhibit VRE, the adjusted ratios made *L. reuteri* as the major strain, and the other three strains as adjuvant strains. FIGS. 12 to 15 show the co-culture results of the VRE and the probiotic combinations of the four strains in different combination ratios. In some embodiments, the four strains of *B. coagulans*, LGG *L. reuteri*, and *L. acidophilus* were combined in four different ratios of 1:1:1:1 (i.e. the contents of the four strains were 25%, 25%, 25%, and 25%, respectively), 1.2:0.5:1.8:0.5 (i.e. the contents of the four strains were 30%, 12.5%, 45%, and 12.5%, respectively), 0.5:0.5:1.8:1.2 (i.e. the contents of the four strains were 12.5%, 12.5%, 45%, and 30%, respectively), and 0.5:1.2:1.8:0.5 (i.e. the contents of the four strains were 12.5%, 30%, 45%, and 12.5%, respectively). In other words, the contents of *B. coagulans*, LGG, *L. reuteri*, and *L. acidophilus* were 12.5%-30%, 12.5%-30%, 25%-45%, and 12.5%-30%, respectively.

Figure 12:
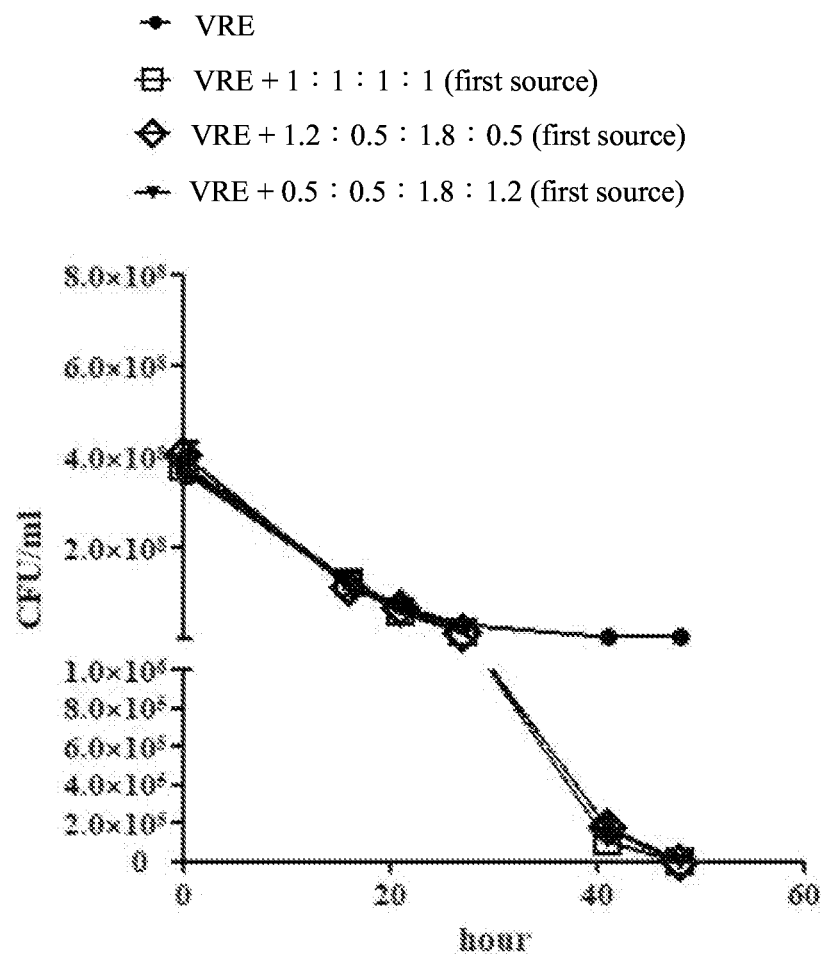
FIGS. 12 to 15 show the co-culture results of the VRE and the probiotic combinations of the four strains in different combination ratios.
Figure 13:
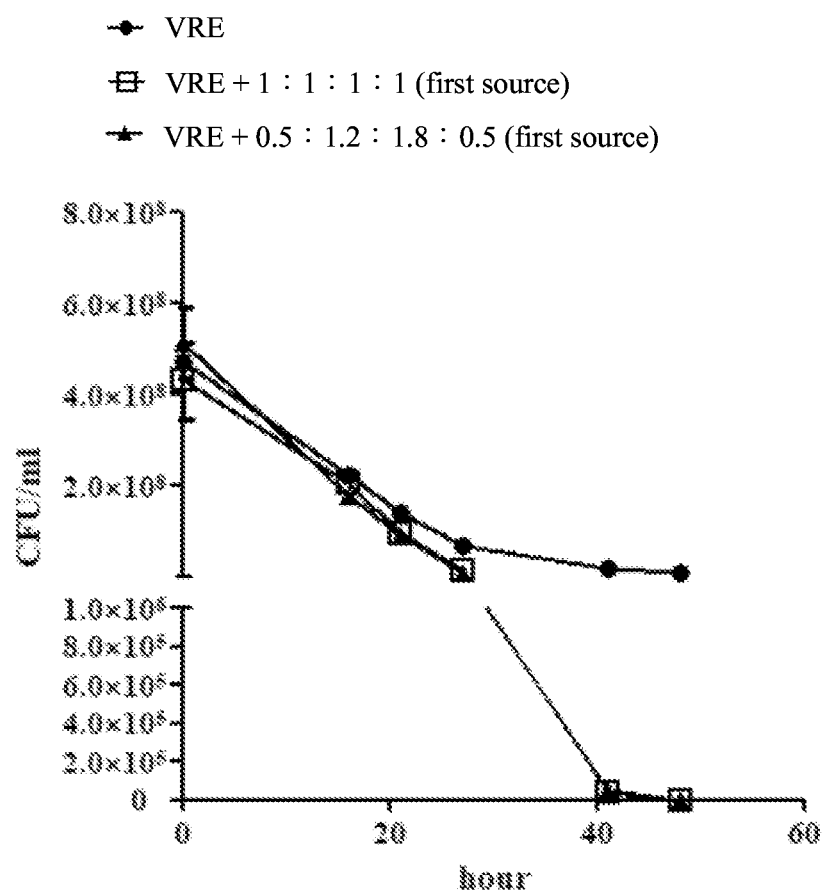
Figure 14:
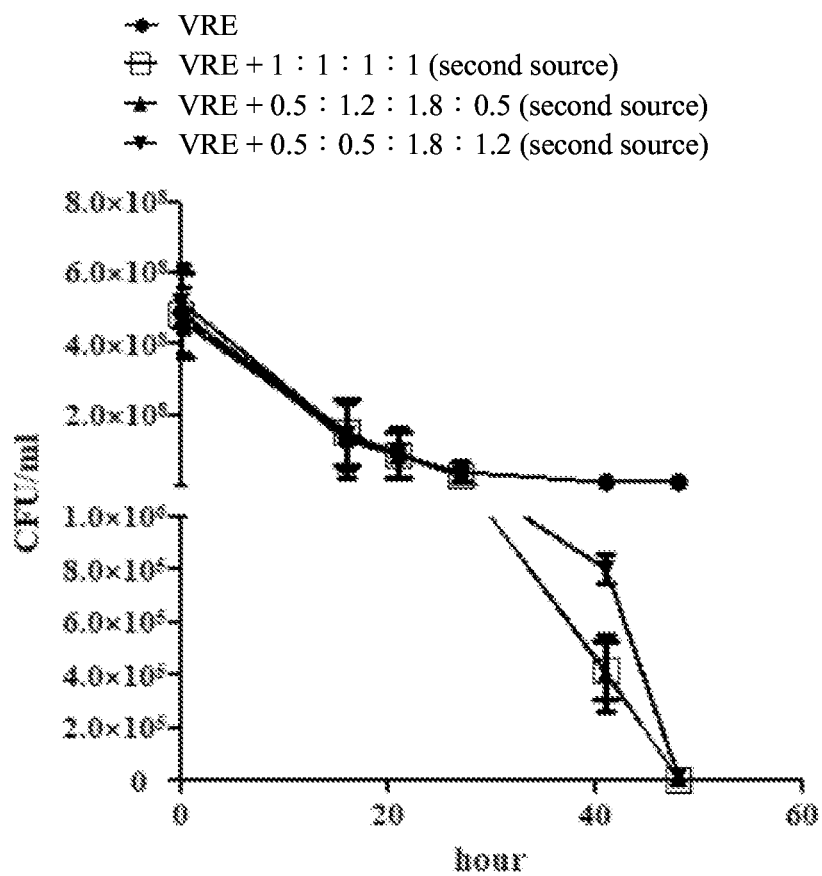
Figure 15:
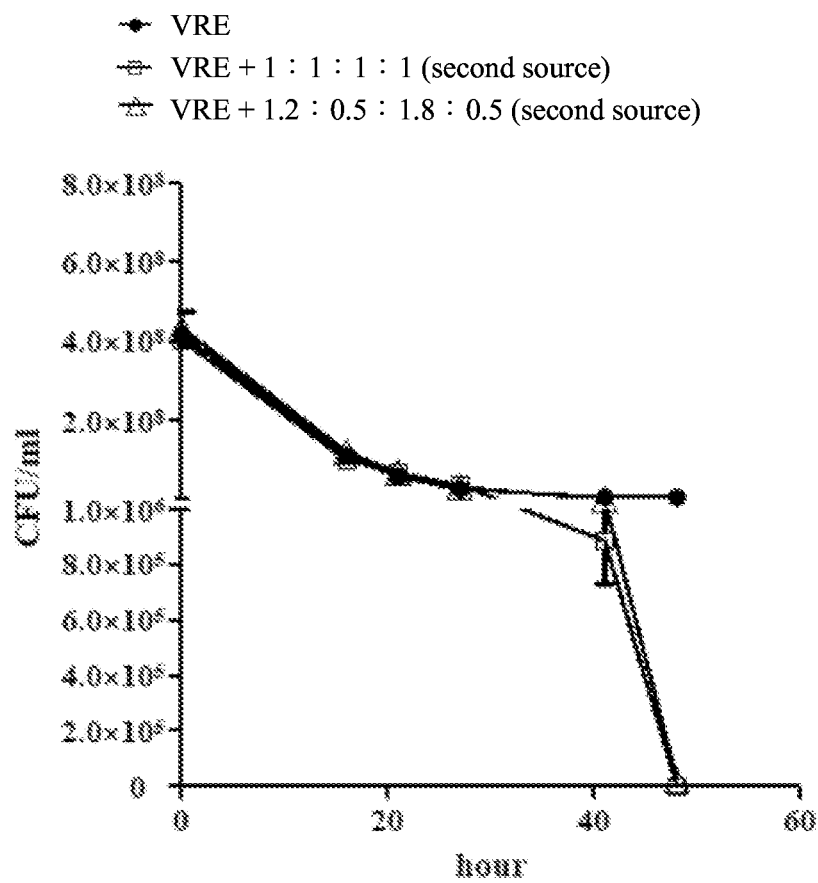

As shown in FIGS. 12 and 13, the probiotic combinations including *B. coagulans*_ATCC7050, LGG_Hansen, *L. reuteri*_BioGaia, and *L. acidophilus*_Infloran (indicated by the first source) had similar effects of inhibiting VRE growth in ratios of 1:1:1:1, 1.2:0.5:1.8:0.5, 0.5:0.5:1.8:1.2, or 0.5:1.2:1.8:0.5. As shown in FIGS. 14 and 15, the probiotic combinations including *B. coagulans*_BC1031, LGG_DSMZ32250, *L. reuteri*_BR101, and *L. acidophilus*_LA1063 (indicated by the second source) had similar inhibitory effects on VRE growth in ratios of 1:1:1:1 and 0.5:1.2:1.8:0.5, whereas the inhibitory effect of the probiotic combination in ratio of 0.5:0.5:1.8:1.2 was slightly inferior, and the inhibitory effect of the probiotic combination in ratio of 1.2:0.5:1.8:0.5 was also slightly inferior to that of the probiotic combination in ratio of 1:1:1:1 at the time point of 41 hour.

According to the results of the above experiments, the probiotic combination including 12.5%-30% *B. coagulans*, 12.5%-30% LGG, 25%-45% *L. reuteri*, and 12.5%-30% *L. acidophilus* has a significant inhibitory effect on VRE growth, and generally the probiotic combination in equal ratio has a better inhibitory effect on VRE growth. Since the probiotic combinations in the above ratios all have significant inhibitory effects on VRE growth and the inhibitory effects are not obviously affected by different combination ratios, so it is reasonably concluded that the probiotic combinations, no matter in equal ratio or unequal ratios, can effectively inhibit the growth of the VRE. The combination ratios in the above embodiments are only used to demonstrate the possible practical ratios but not intended to limit the present invention, so other combination ratios of the same four strains are not deviated from the protection scope of the present invention.

On the other hand, the present invention further analyzed the effect of the probiotic combination including *B. coagulans*, LGG, *L. reuteri*, and *L. acidophilus* on the expressions of the virulence genes acm and asa1 during co-culture with VRE. The acm and asa1 genes are mainly involved in the host cell attachment and colonization of *E. faecium* and *E. faecalis*, respectively (Nallapareddy et al. (2003) Molecular Microbiology 47 (6): 1733-1747; Süβmuth et al. (2000) Infection and Immunity 2000: 4900-4906). The bacterial mRNAs were isolated from the samples at the time points of 0 hour and 16 hours during co-culture. Then, quantitative real-time polymerase chain reaction (qRT-PCR) was performed to quantify the expression levels of the acm gene or the asa1 gene. The expression levels at the time point of 16 hours were compared with those at the time point of 0 hour, so as to evaluate the expression change of the two virulence genes of VRE after co-culture with the probiotic combination of the present invention.

Figure 16:
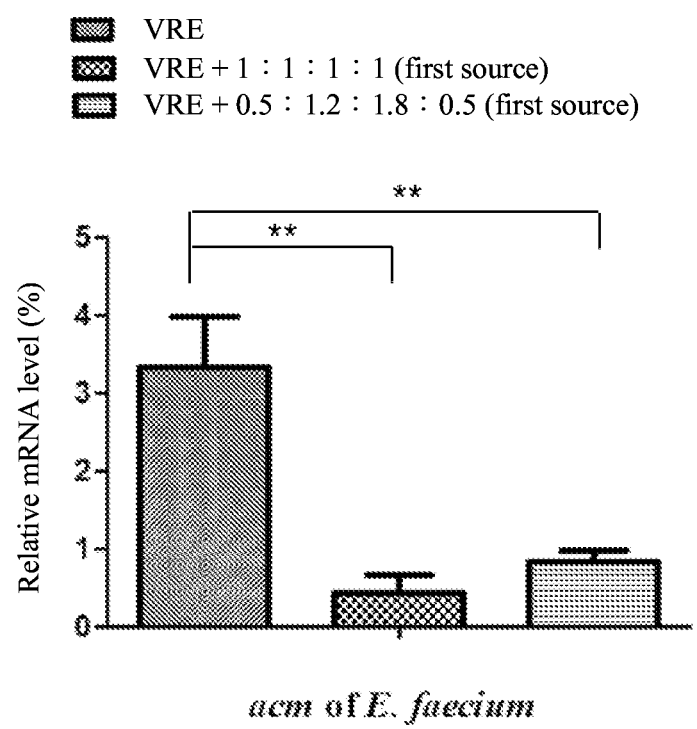
FIG. 16 shows the effect of the probiotic combination from the first source on the expression of the acm gene of *E. faecium*.
Figure 17:
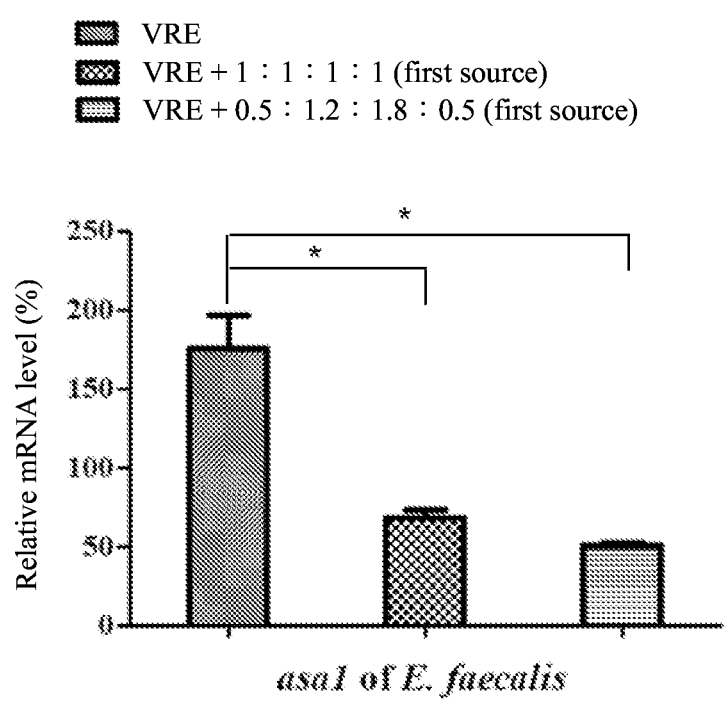
FIG. 17 shows the effect of the probiotic combination from the first source on the expression of the asa1 gene of *E. faecalis*.
Figure 18:
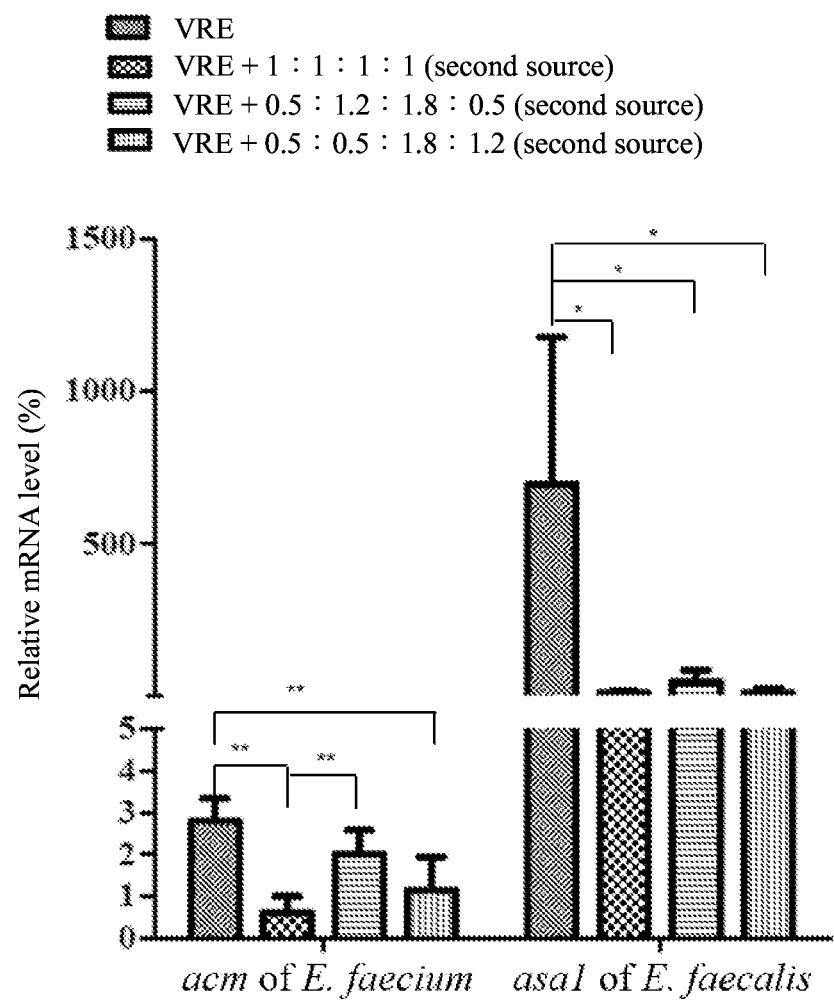
FIG. 18 shows the effect of the probiotic combination from the second source on the acm gene of *E. faecium* and the asa1 gene of *E. faecalis*.

FIG. 16 shows the effect of the probiotic combination from the first source on the expression of the acm gene of *E. faecium*. FIG. 17 shows the effect of the probiotic combination from the first source on the expression of the asa1 gene of *E. faecalis*. FIG. 18 shows the effect of the probiotic combination from the second source on the acm gene of *E. faecium* and the asa1 gene of *E. faecalis*. From the results of the figures, the probiotic combinations including *B. coagulans*_ATCC7050, LGG_Hansen, *L. reuteri*_BioGaia, and *L. acidophilus*_Infloran (first source) effectively inhibited the expression levels of the acm gene and the asa1 gene in ratios of 1:1:1:1 and 0.5:1.2:1.8:0.5, and both ratios showed similar inhibitory effects. The probiotic combinations including *B. coagulans*_BC1031, LGG_DSMZ32250, *L. reuteri*_BR101, and *L. acidophilus*_LA1063 (second source) effectively inhibited the expression levels of the acm gene in ratios of 1:1:1:1 and 0.5:0.5:1.8:1.2. As to the effect on the asa1 gene, the probiotic combinations from the second source effectively inhibited the expression levels of the asa1 gene in ratios of 1:1:1:1, 0.5:1.2:1.8:0.5, and 0.5:0.5:1.8:1.2. Therefore, the probiotic combinations provided in the present invention directly and effectively inhibited the expressions of the virulence genes acm and asa1 of VRE. Since the acm gene and the asa1 gene are involved in the host cell attachment and colonization of VRE, the inhibition on the expressions of the acm gene and the asa1 gene can facilitate the decolonization of VRE from the human gut, and thus reduce the harm of VRE to the human body.

Figure 19:
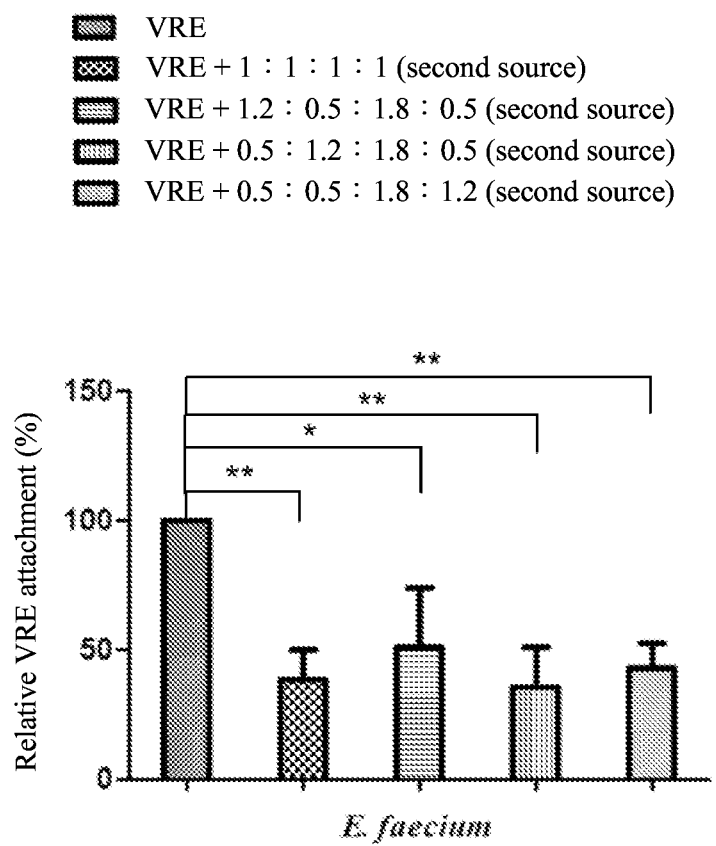
FIG. 19 shows the effects of the probiotic combinations in different ratios on the attachment of *E. faecium* to epithelial cells by competition assay.

In addition, the present invention also investigated the effect of the probiotic combination including *B. coagulans*, LGG, *L. reuteri*, and *L. acidophilus* on VRE attachment to human intestinal epithelial cells. The effect was evaluated by competition assay. In the presence of human intestinal epithelial Caco-2 cells, the probiotic combination and the VRE were simultaneously added for co-culture, so as to observe the effect of the probiotic combination on competing VRE from attaching to Caco-2 cells. In an exemplary experiment, to simplify the experimental design, only *E. faecium*, which clinically showed significant resistance to vancomycin, was used as a representative of VRE in the experiment. The probiotic combinations of the present invention were co-cultured with *E. faecium* and Caco-2 cells, and FIG. 19 shows the effects of the probiotic combinations in different ratios on the attachment of *E. faecium* to epithelial cells by competition assay. From the results of FIG. 19, the probiotic combinations including *B. coagulans*_BC1031, LGG_DSMZ32250, *L. reuteri*_BR101, and *L. acidophilus*_LA1063 (second source) effectively reduced the number of the VRE attaching to Caco-2 cells in a competitive manner in ratios of 1:1:1:1, 1.2:0.5:1.8:0.5, 0.5:1.2:1.8:0.5, and 0.5:0.5:1.8:1.2. That is, the probiotic combinations in different ratios provided in the present invention can significantly reduce the VRE attachment to human intestinal epithelial cells.

On the other hand, the present invention also attempted to compare the effects on reducing VRE attachment to intestinal epithelial cells between the probiotic combinations of the four strains and the individual single strains. The experiments used both competition assay and displacement assay. In the competition assay, the probiotics and the VRE were simultaneously added to the intestinal epithelial cells for co-culture, and after a period of time, the number of the VRE attaching to intestinal epithelial cells was counted against that of the control group without probiotic administration to determine whether the probiotics could reduce the VRE attachment to host cells. While in the displacement assay, the VRE and the intestinal epithelial cells were first co-cultured for a period of time, then the probiotics were added for a further period of time, and finally the numbers of the VRE attaching to intestinal epithelial cells were counted against that of the control group without probiotic administration to determine whether the subsequently added probiotics could reduce the attachment of VRE which was added previously and already attached to the intestinal epithelial cells. The intestinal epithelial cells used in this experiment were the human intestinal epithelial cell line Caco-2 cells, and the VRE strain was E. faecium.

Figure 20:
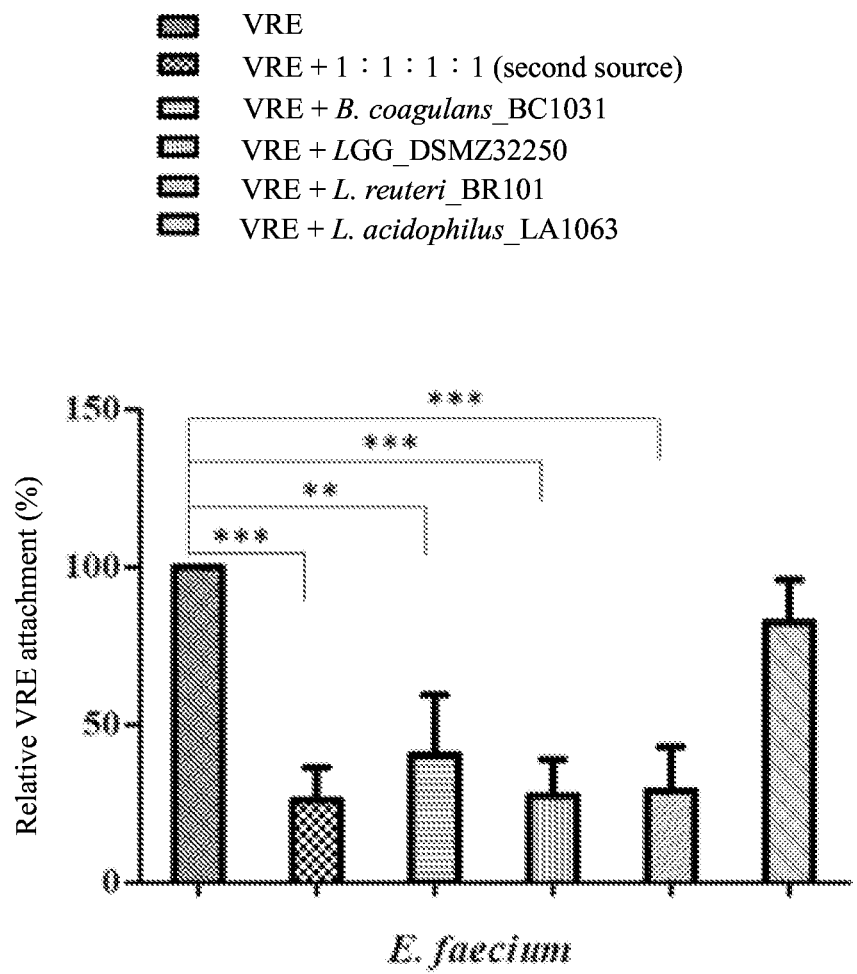
FIG. 20 shows the effects of different probiotics on the attachment of *E. faecium* to epithelial cells by competition assay.
Figure 21:
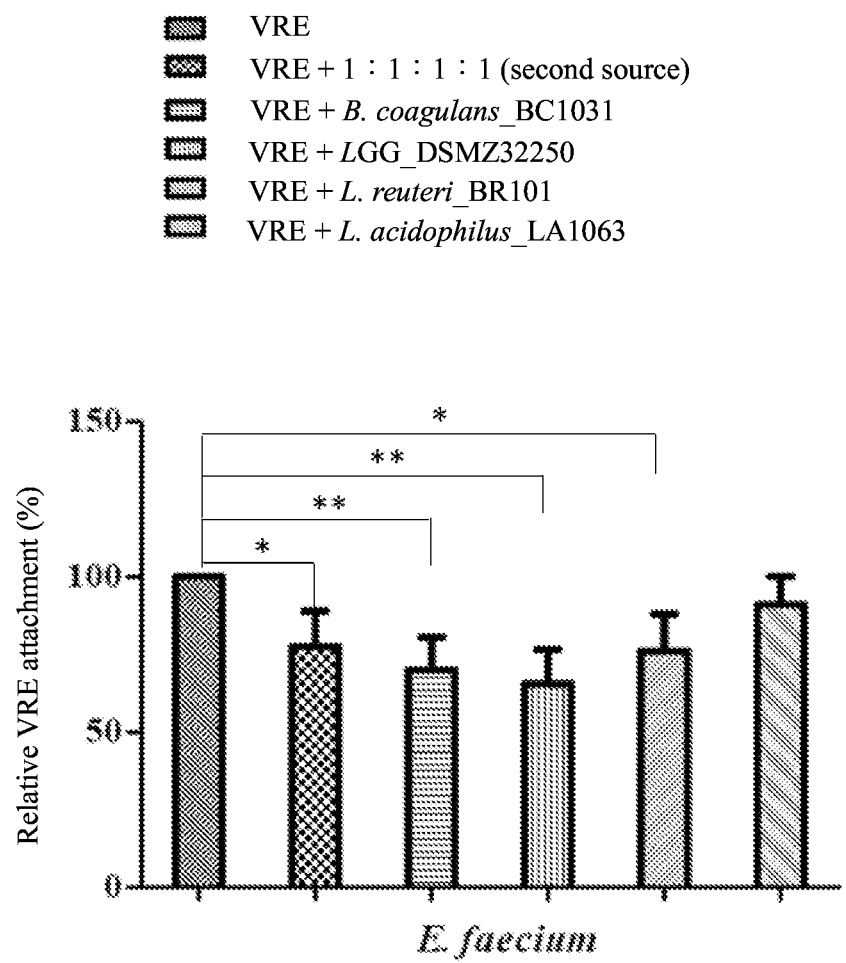
FIG. 21 shows the effects of different probiotics on the attachment of *E. faecium* to epithelial cells by displacement assay.
Figure 22:
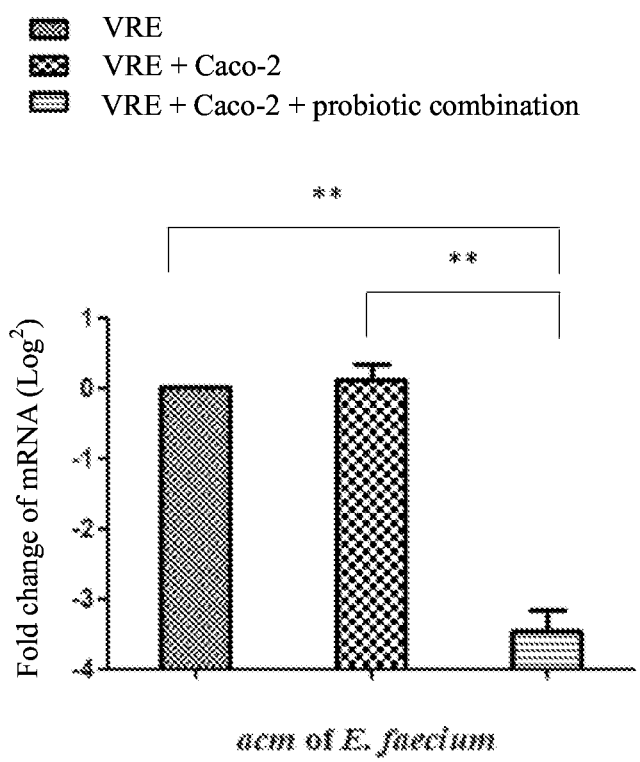
FIGS. 22 to 30 show the effects of the probiotic combination on the virulence genes of *E. faecium* in the presence of host cells.
Figure 23:
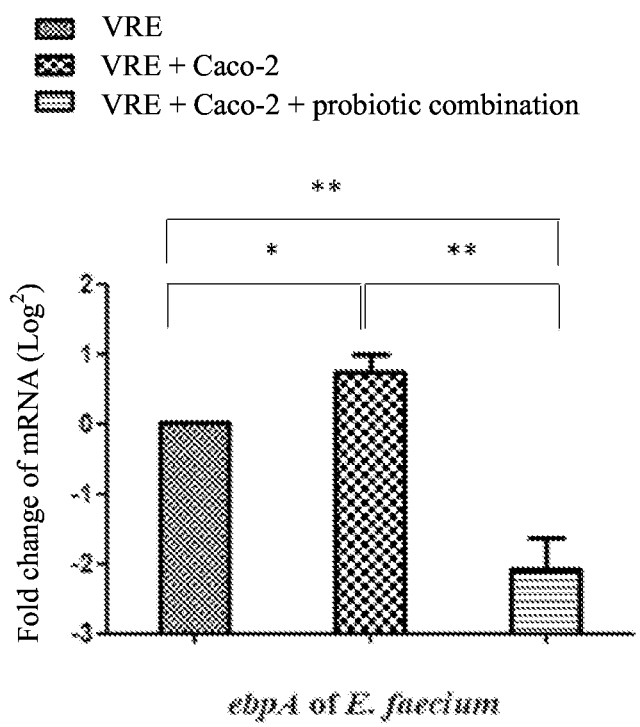
Figure 24:
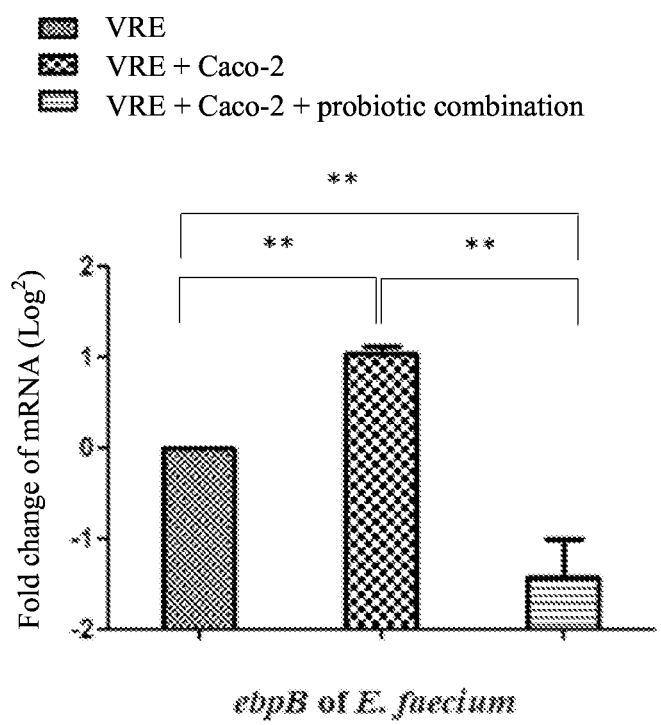
Figure 25:
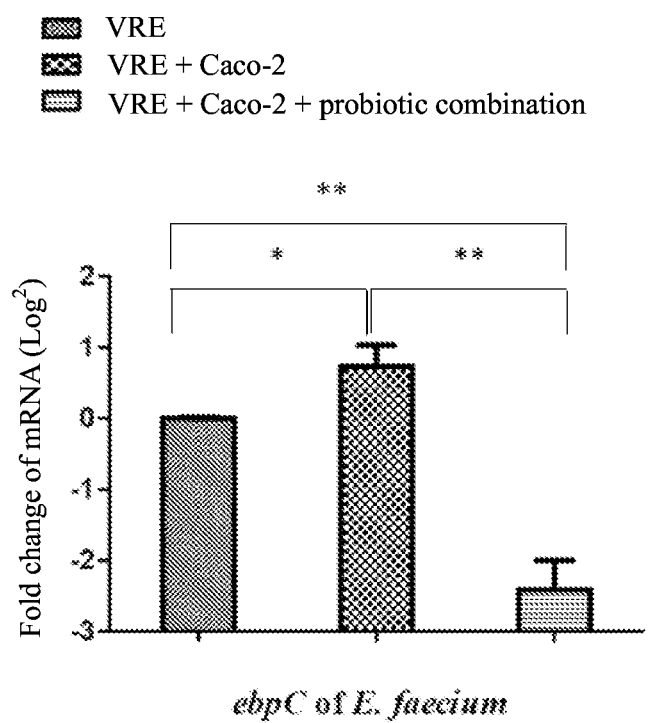
Figure 26:
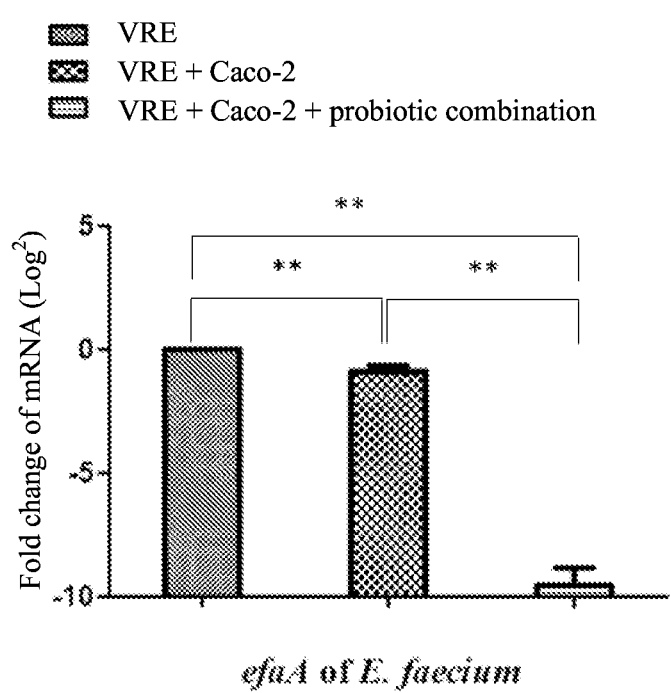
Figure 27:
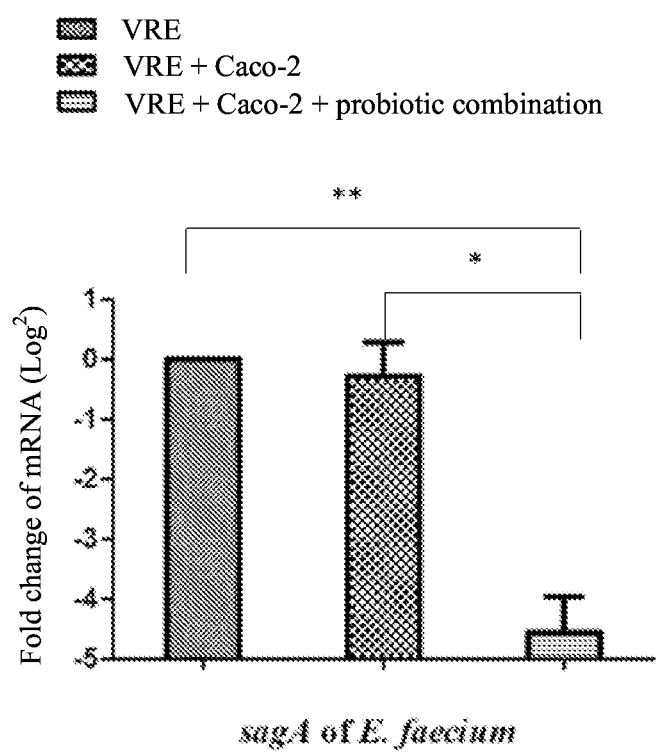
Figure 28:
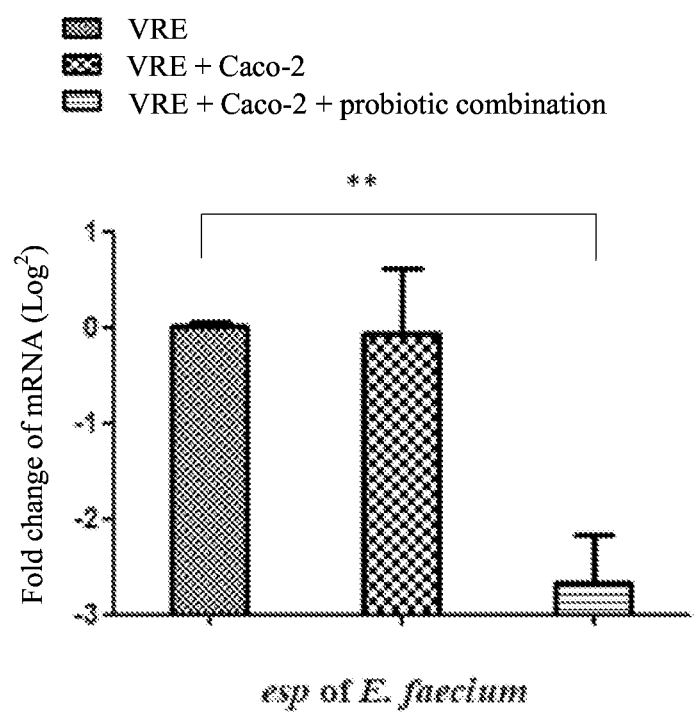
Figure 29:
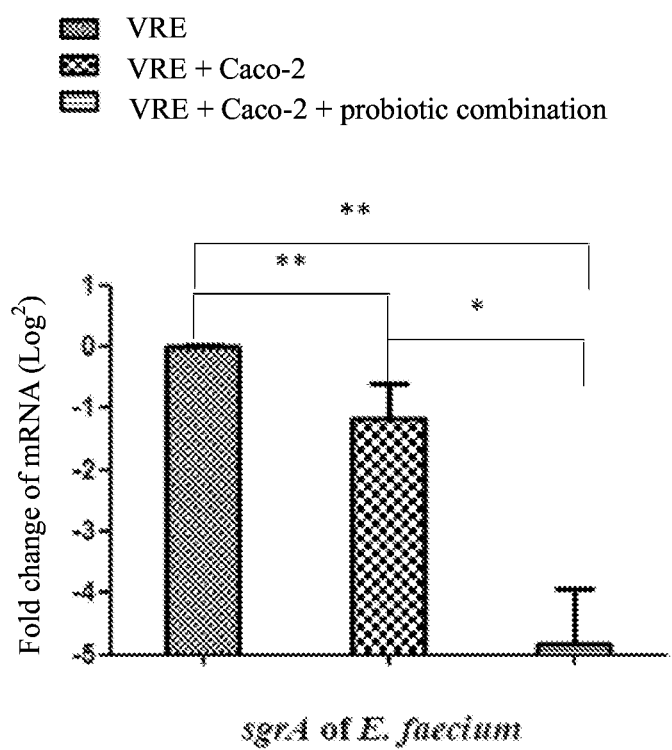
Figure 30:
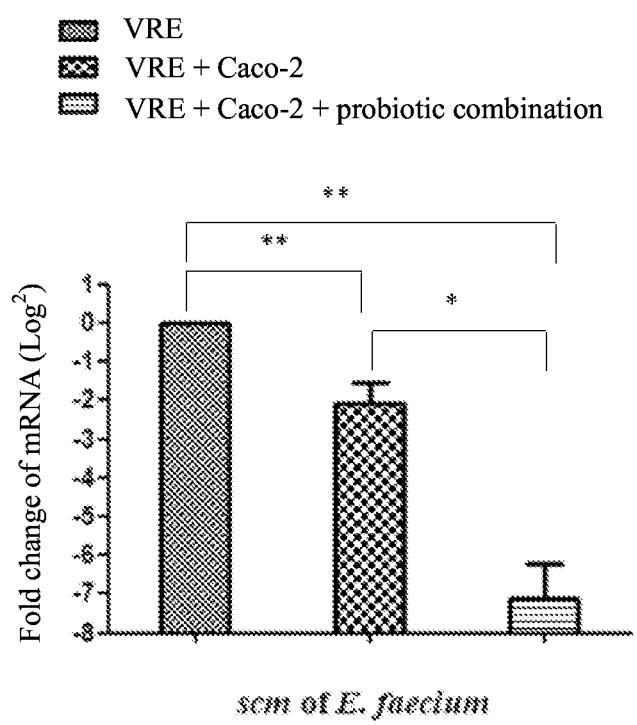

FIG. 20 shows the effects of different probiotics on the attachment of E. faecium to epithelial cells by competition assay. FIG. 21 shows the effects of different probiotics on the attachment of E. faecium to epithelial cells by displacement assay. From the results of FIG. 20, the probiotic combination of four strains from the second source in equal ratio, the single strain of B. coagulans_BC1031, the single strain of LGG_DSMZ32250, and the single strain of L. reuteri_BR101 all reduced the number of E. faecium attaching to Caco-2 cells. The numbers in the individual groups were reduced to 30% to 40% of the control group without probiotic administration, and there were no significant differences between these groups. The single strain of L. acidophilus_LA1063 did not significantly reduce the E. faecium attachment to Caco-2 cells. Further, from the results of FIG. 21, the probiotic combination of four strains from the second source in equal ratio, the single strain of B. coagulans_BC1031, the single strain of LGG_DSMZ32250, and the single strain of L. reuteri_BR101 all reduced the number of E. faecium attaching to Caco-2 cells. The numbers in individual groups were reduced to 65% to 77% of the control group without probiotic administration, and there were no significant differences between these groups. The single strain of L. acidophilus_LA1063 did not significantly reduce the E. faecium attachment to Caco-2 cells. According to the foregoing experiments, besides the probiotic combination of four strains significantly reduced the attachment of VRE to the host cells, the individual single strains of B. coagulans, LGG and L. reuteri also significantly reduced the attachment of VRE to the host cells.

In order to figure out why the probiotic combination could affect the VRE attachment to the host cells, the present invention further investigated the expression levels of the VRE virulence genes, which are involved in VRE host cell attachment and biofilm formation, after co-culture of VRE and the intestinal epithelial cell line Caco-2. The nine virulence genes analyzed include acm, ebpA, ebpB, ebpC, efaA, sagA, esp, sgrA, and scm, and it was to observe whether the addition of the probiotic combination affects the expression levels of these VRE virulence genes. In an exemplary experiment, the probiotic combination was prepared by mixing B. coagulans_BC1031, LGG_DSMZ32250, L. reuteri_BR101, and L. acidophilus_LA1063 (second source) in equal ratios, and was co-cultured with E. faecium and the human intestinal epithelial Caco-2 cells for 2.5 hours. Then, the samples were collected to quantify the expression levels of the virulence genes.

FIGS. 22 to 30 show the effects of the probiotic combination on the virulence genes of E. faecium in the presence of host cells. The experiment included three groups, which were the control group (VRE only), the co-culture group of VRE and Caco-2 (VRE+Caco-2), and the co-culture group of VRE, Caco-2 and the probiotic combination (VRE+Caco-2+probiotic combination), and the expression levels of the virulence genes were compared between the co-culture group of VRE+Caco-2 and the control group, and also between the co-culture group of VRE+Caco-2 and the co-culture of VRE+Caco-2+probiotic combination. The expression levels of the virulence genes were calculated against that of the control group and displayed as $\log^2$ value. From FIGS. 23 to 25, it was observed that when VRE was co-cultured with Caco-2 (VRE+Caco-2), the expression levels of the ebpA, ebpB, and ebpC genes were increased to approximately 2-fold change. On the other hand, from FIGS. 22 to 30, it was observed that the expression levels of the nine genes acm, ebpA, ebpB, ebpC, efaA, sagA, esp, sgrA, and scm were significantly decreased when the probiotic combination was added for co-culture, and this may be the reason why the simultaneously added probiotic combination reduced the number of VRE attaching to Caco-2 cells in the competition assay. In other words, the probiotic combination of the present invention has the down-regulating (inhibiting) effect on the expressions of the VRE virulence genes, and thus can effectively reduce the VRE attachment to the host cells, which facilitates decolonizing VRE from the host gut, reducing the virulence of VRE, and further reducing the harm of VRE to the human body.

Therefore, the probiotic combination provided in the present invention can significantly inhibit the growth, host cell attachment, or virulence of VRE, and thus can be further developed into a medicine and health product to effectively prevent or treat VRE infection. For example, the probiotic combination provided in the present invention can be further prepared as a probiotic capsule, which includes the four strains of B. coagulans, LGG, L. reuteri and L. acidophilus, and an excipient. In an embodiment, the four strains are combined in equal ratio, and the excipient is corn starch but not limited thereto. In some other embodiments, the four strains are combined with the contents of 12.5%-30%, 12.5%-30%, 25%-45%, and 12.5%-30%, respectively, and the excipient is corn starch but not limited thereto. In addition to administrating the probiotic combination to treat VRE infection after VRE infection, the probiotic combination can also be administrated to prevent VRE infection when the patient is hospitalized or immunocompromised. Evan more, the daily administration of the probiotic combination may promote the intestinal health.

Accordingly, the present invention further provides a method for inhibiting growth, host cell attachment, and virulence of VRE by administrating the probiotic combination including B. coagulans, LGG, L. reuteri, and L. acidophilus. The present invention also provides a method for inhibiting virulence gene expression of VRE by administrating the probiotic combination including B. coagulans, LGG, L. reuteri, and L. acidophilus, wherein the virulence gene includes at least one of asa1, acm, ebpA, ebpB, ebpC, efaA, sagA, esp, sgrA, and scm genes.

It is to be noted that the most important spirit of the present invention is to use the microbial network analysis driven by rule-based microbial network algorithm to select the probiotic combination which can effectively inhibit the growth of VRE, and perform biological experiments to verify the inhibitory effects of the probiotic combination. The combination ratios of the four stains in the above embodiments are only used to demonstrate the possible practical ratios but not intended to limit the present invention, and other combination ratios of the same four strains are not deviated from the protection scope of the present invention.

In addition, except that the probiotic combination of four strains can effectively inhibit the growth, host cell attachment, or virulence of VRE, the individual single strain of *B. coagulans*, LGG, *L. reuteri*, or *L. acidophilus* may also have effect of inhibiting the growth, host cell attachment, or virulence of VRE. For example, as shown in FIGS. 8 to 11, the individual single strain of LGG, *L. reuteri* or *L. acidophilus* inhibited the VRE growth. Also, as shown in FIGS. 20 and 21, the individual single strains of *B. coagulans*, LGG, or *L. reuteri* inhibited the VRE attachment to the host cells. Therefore, the efficacy of the individual single probiotic strain to inhibit VRE should be also covered by the scope of the present invention.

In conclusion, the present invention used the microbial network analysis combined with biological experiments to select the probiotic combination which can effectively inhibit the VRE growth. The probiotic combination includes the four strains of *B. coagulans*, LGG, *L. reuteri*, or *L. acidophilus*. The probiotic combination can effectively inhibit VRE growth in vitro. The four probiotic strains are not limited to the strains from specific sources, and the combination ratio of the four probiotic strains is not limited. In addition, the probiotic combination can reduce VRE attachment to human intestinal epithelial cells, and significantly inhibit expressions of VRE virulence genes, including asa1, acm, ebpA, ebpB, ebpC, efaA, sagA, esp, sgrA, and scm. From the above, the probiotic combination provided in the present invention can effectively inhibit the growth, host cell attachment, or virulence of VRE, and thus can be further developed into a medicine and health product, which will be useful for clinical treatment or prevention, and facilitate decolonizing VRE from the host gut, reducing the virulence of VRE, and further reducing the harm of VRE to the human body While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A method for inhibiting growth, host cell attachment, or virulence of vancomycin-resistant enterococci (VRE) by administrating a probiotic combination to a subject in need of treating or preventing VRE infection, wherein the probiotic combination consists of *Bacillus coagulans*, *Lactobacillus rhamnosus* GG, *Lactobacillus reuteri*, and *Lactobacillus acidophilus*.

2. The method according to claim 1, wherein the probiotic combination inhibits virulence gene expression of the vancomycin-resistant enterococci.

3. The method according to claim 2, wherein the virulence gene comprises at least one of asa1, acm, ebpA, ebpB, ebpC, efaA, sagA, esp, sgrA, and scm genes.

4. The method according to claim 1, wherein the probiotic combination inhibits the vancomycin-resistant enterococci from attaching to human intestinal epithelial cells.

5. The method according to claim 1, wherein the vancomycin-resistant enterococci comprise *Enterococcus faecium* and *Enterococcus faecalis*.

6. The method according to claim 1, wherein the probiotic combination is prepared as a probiotic capsule, and the probiotic capsule comprises an excipient.

7. The method according to claim 6, wherein the excipient is corn starch.

* * * * *